United States Patent
Lambrecht et al.

(10) Patent No.: US 6,617,473 B1
(45) Date of Patent: Sep. 9, 2003

(54) PRODUCTION OF DIBENZOSUBERENONE DERIVATIVES BY CATALYTIC DEHYDROGENATION

(75) Inventors: Stefan Lambrecht, Holzminden (DE); Horst Surburg, Holzminden (DE)

(73) Assignee: Haarman & Reimer GmbH (DE)

( * ) Notice: Subject to any disclaimer, the term of this patent is extended or adjusted under 35 U.S.C. 154(b) by 0 days.

(21) Appl. No.: 10/069,888

(22) PCT Filed: Aug. 22, 2000

(86) PCT No.: PCT/EP00/08167

§ 371 (c)(1),
(2), (4) Date: Feb. 26, 2002

(87) PCT Pub. No.: WO01/16065

PCT Pub. Date: Mar. 8, 2001

(30) Foreign Application Priority Data

Aug. 30, 1999 (DE) .......................................... 199 41 211

(51) Int. Cl.$^7$ ............................................... C07C 45/65
(52) U.S. Cl. ...................... 568/312; 568/314; 568/315; 568/321; 568/326; 568/329
(58) Field of Search ................................. 568/312, 311, 568/314, 315, 321, 326, 329

(56) References Cited

U.S. PATENT DOCUMENTS

| | | | |
|---|---|---|---|
| 3,448,102 A | 6/1969 | Yale et al. | 260/239 |
| 3,551,498 A | 12/1970 | Tristram et al. | 260/590 |
| 3,836,585 A | 9/1974 | Tristram et al. | 260/590 |
| 5,313,008 A | * 5/1994 | Newman | |

FOREIGN PATENT DOCUMENTS

| | | |
|---|---|---|
| DE | 298 773 | 3/1992 |
| EP | 0 953 294 | 11/1999 |
| GB | 2132618 | 7/1984 |

OTHER PUBLICATIONS

Methoden den Organischen Chemie, Houben–Weyl, 4$^{th}$ edition, (month unavailable) 1981, vol. V/2b, pp. 107–130, Prof. Dr. Manimilian Zander & Prof Dr. Christoph Grundmann, aus cyclischen Verbindungen.

Tetrahedron, vol. 50, (month unavailable) 1994, pp. 8773–8780, Hermenegildo Garcia, Miguel A. Miranda, Fatemeh Mojarrad and Maria–José Sabater, Involvement of Oxirane Intermediates in the Electron Transfer Photooxygenation of 1,1– and 1,2–Diarylethylenes Sensitized by 2,4,6–Triphenylpyrylium Tetrafluoroborate.

Chem. Ber., Aug. 1989, p. 1595–1597, Dieter Hellwinkel and Thomas Becker, Transannulare Hydridverschiebung versus Cyclokondensation bei 5–(2–Biphenylyl)–10, 11–dihydro–5H–dibenzo[a,d]cyclohepten–5–ol–Derivaten.

J. Chem. Soc. Perkin Trans. 2, (month unavailable) 1993, pp. 1923–1926, Marcella Bonchi, Valeria Conte, Fulvio Di Furia, Tommaso Carofiglio, Franco Magno and Paolo Pastore, Co–Induced Radical Oxidations by Peroxomolybdenum Complexes.

J. Chem. Soc., Chem. Commun., (month unavailable) 1990, pp. 730–732, Kazuo Yanada, Reiko Yanada and Haruo Meguri, Selenium–catalysed Debromination of vic–Dibromides to Alkenes with Cysteine or Glutathione.

Tetrahedron, vol. 50, (month unavailable) 1994, pp. 973–978, Maria Luixa A. von Hollenben, Mônica Zucolotto, Claudia A. Zini and Eduardo R. Oliveria, A Selective Reduction of α,β–Unsaturated Ketones.

* cited by examiner

Primary Examiner—Samuel Barts
Assistant Examiner—Sikarl A. Witherspoon
(74) Attorney, Agent, or Firm—Pendorf & Cutliff

(57) ABSTRACT

The invention relates to a preparation process for derivatives by catalytic dehydrogenation of dibenzosuberone derivatives.

14 Claims, No Drawings

PRODUCTION OF DIBENZOSUBERENONE DERIVATIVES BY CATALYTIC DEHYDROGENATION

FIELD OF THE INVENTION

The invention relates to a preparation process for dibenzosuberenone derivatives by catalytic dehydrogenation of dibenzosuberone derivatives.

BACKGROUND OF THE INVENTION

Dibenzosuberenone (5H-dibenzo[a,d]cyclohepten-5-one) is an important raw material for preparing pharmacologically active compounds.

In the pharmaceutical industry, dibenzosuberenone is used as starting material for various pharmacologically active compounds. These active compounds are, for example, amitriptyline and nortriptyline (E. Mutschler Arzneimittelwirkungen, 6th. Ed., Wiss. Ver.-Ges., Stuttgart, 1991, pp. 120–123). Accordingly, there is a permanent demand for dibenzosuberenone and its derivatives.

Dibenzosuberenone can be obtained for example by bromination of dibenzosuberone with N-bromosuccinimide and elimination of the brominated intermediate (GB-A 2132618, U.S. Pat. No. 3,448,102). The bromination can also be carried out using bromine (Chem. Ber. 1989, 122, 1595–1597). For debromination, there are also various known possibilities. Debromination can be carried out using, for example, sodium selenite (J.Chem.Soc., Chem.Commun. 1990, 730–732) or chromium dichloride (U.S. Pat. No. 3,836,585).

Other possibilities for preparing dibenzosuberenone proceed, for example, photochemically (Tetrahedron 1994, 50, 8773–8780) or involve the use of a complex molybdenum compound (J.Chem.Soc., Perkin Trans. 2, 1993, 1923–1936).

However, these known preparation methods are disadvantageous. Thus, critical starting materials, such as, for example, bromine or sodium selenite, are used, the starting materials are not commercially available in the amounts required or are expensive to prepare, the yields in the reactions are insufficient, the purity of the product is poor (for example residual content of organic halogen compounds), the reaction cannot be carried out on an industrial scale or the starting materials are dangerous to handle.

Dehydrogenation of dibenzosuberone derivatives is known per se as a possibility for preparing dibenzosuberenone derivatives (Acta Chim. Acad. Sci. Hung., 1978, 98, 393). However, no hydrogen acceptor is employed, so that this reaction is a disproportionation of the starting material. As a consequence, the loss of starting material is high and the yield is low.

With the present invention, it was possible to overcome the disadvantages mentioned and to provide a process which is favourable for use in industry.

SUMMARY OF THE INVENTION

This invention, accordingly, provides a process for preparing substituted dibenzosuberenones of the formula

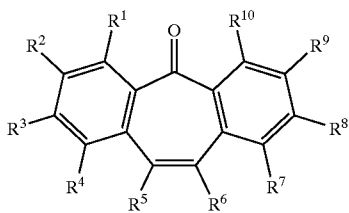

in which,
$R^1$ to $R^{10}$ are identical or different and represent hydrogen, fluorine, chlorine, iodine, bromine, cyano, a straight-chain or branched aliphatic hydrocarbon radical having 1 to 8 carbon atoms, a straight-chain or branched acyl radical having 1 to 8 carbon atoms, a substituted aryl radical, a substituted hetaryl radical, or one of the groups

in which
$R^{11}$ represents a straight-chain or branched alkyl radical having 1 to 8 carbon atoms,
$R^{12}$ represents a straight-chain or branched alkyl radical or acyl radical having 1 to 8 carbon atoms and
X and Y are identical or different and represent

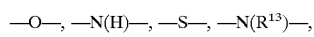

where
$R^{13}$ represents a straight-chain or branched alkyl radical having 1 to 8 carbon atoms,
characterized in that dibenzosuberones of the formula

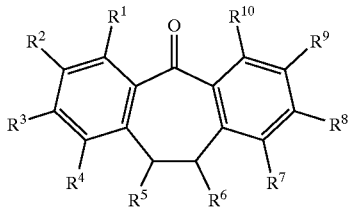

in which
$R^1$ to $R^{10}$ are each as defined above are catalytically dehydrogenated.

DETAILED DESCRIPTION OF THE INVENTION

The practice of the process according to the invention, with the use of unobjectionable reagents, is without problems. Moreover, commercially available starting materials are employed. The end product does not contain any undesirable halogen-containing by-products.

Straight-chain or branched aliphatic hydrocarbon radicals ($R^1$ to $R^{13}$) generally contain 1 to 8, preferably 1 to 6, particularly preferably 1 to 4, carbon atoms. The following radicals may be mentioned specifically: methyl, ethyl, propyl, iso-propyl, butyl, iso-butyl, pentyl, iso-pentyl, hexyl, iso-hexyl, heptyl, iso-heptyl, octyl and iso-octyl. Preference is given to methyl, ethyl, propyl, iso-propyl, butyl, iso-butyl. Straight-chain or branched aliphatic acyl radicals ($R^1$ to $R^{12}$) generally contain 1 to 8, preferably 1 to 6, particularly preferably 1 to 4, carbon atoms. Preference is given to: acyl, propionyl, butyryl, iso-butyryl.

Aryl radicals are, in general, aromatic, cyclic hydrocarbon radicals having 6 carbon atoms. It is possible for a plurality, for example 2 or 3, of the radicals to be fused into one radical. Preference is given to: phenyl, naphthyl.

Hetaryl radicals are, in general, aromatic, cyclic hydrocarbon radicals having 2 to 5 carbon atoms and one or more, preferably one, heteroatom. Possible heteroatoms are, for example, nitrogen, oxygen and sulphur, preferably nitrogen. It is possible for a plurality, for example 2 or 3, of the aryl and hetaryl radicals to be fused into one radical. The following radicals may be mentioned specifically: furan, thiophene, pyrrole, pyridine, pyrazine, pyrimidine, indole, quinoline, iso-quinoline. Preference is given to furan, thiophene, pyrrole, pyridine.

Possible substituents of aryl and hetaryl radicals are, for example: alkyl, acyl, $OR^{13}$, $NR^{13}$, halogen atoms.

The group $X$—$C(=O)$—$Y$—$R^{11}$ can, for example, be: methyl carbamate, methyl carbonate, ethyl carbamate, ethyl carbonate.

Dibenzosuberones for the process according to the invention are compounds of the formula

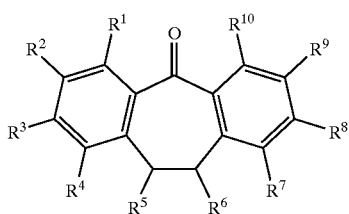

in which
$R^1$ to $R^{10}$ are each as defined above.

The dibenzosuberones for the process according to the invention are known per se (J. Org. Chem. 1994, 59, 7968–75).

Catalytically acting elements of the 8th transition group are, for example, platinum, palladium, ruthenium and rhodium. Preference is given to palladium.

Supports for the catalytically acting elements of the 8th transition group are, for example, activated carbon and alumina. Preference is given to activated carbon.

In general, catalysts comprising 0.5 to 15% by weight, preferably 1 to 10% by weight, of an element of the 8th transition group are used for the process according to the invention.

The α,β-unsaturated carbonyl compounds used are compounds such as fumaric esters, maleic esters, mesityl oxide, benzal acetone, isophorone, verbenone, crotonic esters, and the like. Particular preference is given to using dehydrogenating agents whose solubility characteristics in the liquid phase are such that separation of excess dehydrogenating agent and its reaction products in the crystallization is complete, for example dibutyl maleate.

For the process according to the invention, the α,β-unsaturated carbonyl compound is employed in a ratio of from 0.2 to 10 parts by weight, based on 1 part by weight of the starting material.

The α,β-unsaturated carbonyl compounds are preferably employed in excess, thus acting simultaneously as solvent. Use of a further solvent can therefore be dispensed with.

The dehydrogenation by the process according to the invention is preferably carried out in liquid phase. The liquid phase used is the reaction mixture.

The process according to the invention is generally carried out in a temperature range from 100 to 300° C. If dibutyl maleate is used, the process is preferably carried out at 220–260° C. The process can be carried out under atmospheric pressure and under elevated or reduced pressure. By way of example, the following pressure range may be mentioned: 0.2 to 10 bar.

The amount of catalyst can be from 0.001 to 30% by weight, preferably from 0.2 to 15% by weight, based on the starting material.

The process according to the invention can be illustrated by the following formula scheme:

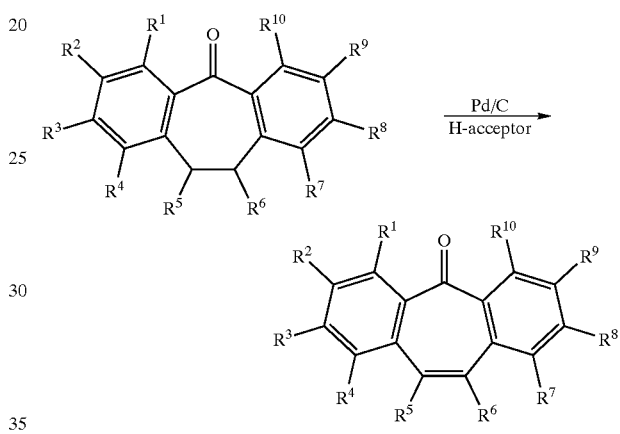

The process according to the invention can be carried out, for example, as follows: dibenzosuberone is reacted with 10% by weight of Pd/C (10% by weight of Pd) and 1.5 times the amount (based on the weight) of dibutyl maleate. After the reaction, the mixture is filtered off, the dehydrogenating agent is distilled off and the product is purified by crystallization.

The preparation of aromatic compounds from saturated and partially saturated precursors by catalytic dehydrogenation is a procedure known per se in organic chemistry (Methoden d. Org. Chemie (Houben-Weyl), 4th edition 1981, Vol. 5/2b, pp. 107–130). The use of α,β-unsaturated carbonyl compounds as hydrogen acceptor has likewise been described (Tetrahedron, 1994, 50, 973–978). This method has also been described for aromatizing 2(3H)-benzofuranones from the corresponding partially hydrogenated precursors (DE-A 19 909 980). Dehydrogenation of dibenzosuberone derivatives is known per se as a possibility for preparing dibenzosuberenone derivatives (Acta Chim. Acad. Sci. Hung., 1978, 98, 393). However, no hydrogen acceptor is employed, so that this reaction is really a disproportionation of the starting material. As a consequence, the loss of starting material is high and the yield is low.

The process according to the invention is preferably employed for preparing dibenzosuberenone of the formula

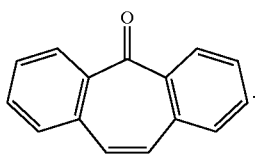

The process according to the invention was surprising, since the disproportionation, which takes place as a competing reaction, is suppressed almost completely by addition of a hydrogen acceptor. As a consequence, the yield is improved considerably. Moreover, none of the starting material is converted into a by-product which cannot be utilized further. In addition, the hydrogen acceptor is uncritical with respect to toxicity and handling, owing to which industrial realization would be possible in the first place.

EXAMPLES

Example 1

Preparation of dibenzosuberenone by catalytic dehydrogenation using dibutyl maleate as hydrogen acceptor.

Under nitrogen, 500 g of dibenzosuberone, 792 g of dibutyl maleate, 125 g of cyclohexane and 25 g of palladium 5% by weight on activated carbon are heated to 220° C. During heating-up, the cyclohexane distils off. The reaction mixture is heated at 220° C. for 6 hours.

The mixture is subsequently filtered at 80° C., the esters are distilled off and the crude product is recrystallized from ethanol.

Yield: 72%
Purity: 99.1% (GC)
Melting point: 89° C.

Example 2

20 mg of methyl 5-oxo-10,11-dihydro-5H-dibenzo[a,d]cycloheptene-4-carboxylate, 2.7 g of dibutyl maleate and 100 mg of palladium 5% by weight on activated carbon are combined and stirred at 210° C. for 4 hours. The mixture is then diluted with acetone, filtered and concentrated.

Gas chromatographic analysis shows a ratio of methyl 5-oxo-10,11-dihydro-5H-dibenzo[a,d]cycloheptene-4-carboxylate to methyl 5-oxo-5H-dibenzo[a,d]cycloheptene-4-carboxylate of 1.4 to 1.

Methyl 5-oxo-5H-dibenzo[a,d]cycloheptene-4-carboxylate:

| m/e | Intensity/% |
|---|---|
| 233 | 100 |
| 176 | 60.5 |
| 264 | 50.6 |
| 88 | 47.2 |
|  | 26 |
| 123 | 25 |
| 108 | 21 |
| 39 | 17 |
| 82 | 19 |
| 109 | 18 |

What is claimed is:

1. A process for preparing substituted dibenzosuberenones of the formula

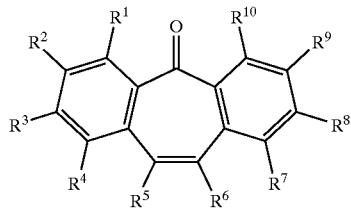

in which
$R^1$ to $R^{10}$ are identical or different and represent hydrogen, fluorine, chlorine, bromine, cyano, iodine, a straight-chain or branched aliphatic hydrocarbon radical having 1 to 8 carbon atoms, a straight-chain or branched acyl radical having 1 to 8 carbon atoms, a substituted aryl radical, a substituted hetaryl radical, or one of the groups

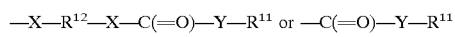

in which
$R^{11}$ represents a straight-chain or branched alkyl radical having 1 to 8 carbon atoms,
$R^{12}$ represents a straight-chain or branched alkyl radical or acyl radical having 1 to 8 carbon atoms and
X and Y are identical or different and represent

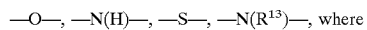

$R^{13}$ represents a straight-chain or branched alkyl radical having 1 to 8 carbon atoms,
comprising the step of catalytically dehydrogenating dibenzosuberones of the formula,

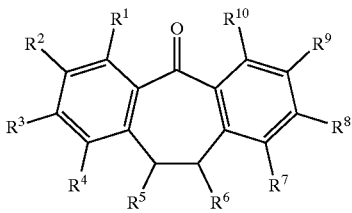

in which,
$R^1$ to $R^{10}$ are each as defined above, in the presence of from 0.001 to 30% by weight, based on the starting material, of a catalyst comprising an element of the 8th transition group, which is optionally supported, and from 0.2 to 10 parts by weight, based on one part by weight of starting material, of α,β-unsaturated carbonyl compounds as hydrogen acceptors.

2. A process according claim 1, wherein the element of the 8th transition group used is palladium.

3. A process according to claim 1, wherein the support used for the elements of the 8th transition group is activated carbon or carbon.

4. A process according to claim 1, wherein the α,β-unsaturated carbonyl compounds used are esters of fumaric or maleic acid.

5. A process according to claim 1, wherein the α,β-unsaturated carbonyl compounds used are dibutyl esters of fumaric or maleic acid.

6. A process according to claim 1, wherein the dehydrogenation is carried out using 0.001 to 30% by weight of palladium, based on the starting material, on activated carbon (5–15% by weight) and dibutyl esters of fumaric or maleic acid as hydrogen acceptors, at from 100 to 300° C.

7. A process according to claim 6, wherein the dehydrogenation is carried out using 0.2 to 15% by weight of palladium, based on the starting material, on activated carbon (5–15% by weight) and dibutyl esters of fumaric and maleic acid as hydrogen acceptors, at from 200 to 260° C.

8. A process according to claim 7, wherein the dehydrogenation is carried out using 1 to 10% by weight of palladium, based on the starting material, on activated carbon (5–15% by weight) and dibutyl maleate as hydrogen acceptor, at 220–260° C.

9. A process for preparing substituted dibenzosuberenones of the formula

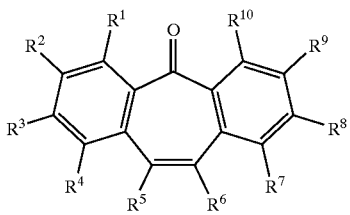

in which
R$^1$ to R$^{10}$ are identical or different and represent hydrogen, fluorine, chlorine, bromnine, cyano, iodine, a straight-chain or branched aliphatic hydrocarbon radical having 1 to 8 carbon atoms, a straight-chain or branched acyl radical having 1 to 8 carbon atoms, a substituted aryl radical, a substituted hetaryl radical, or one of the groups

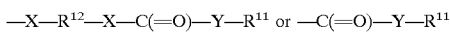

in which
R$^{11}$ represents a straight-chain or branched alkyl radical having 1 to 8 carbon atoms,
R$^{12}$ represents a straight-chain or branched alkyl radical or acyl radical having 1 to 8 carbon atoms and
X and Y are identical or different and represent

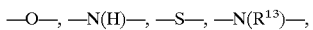

where
R$^{13}$ represents a straight-chain or branched alkyl radical having 1 to 8 carbon atoms,
comprising, the step of catalytically dehydrogenating dibenzosuberones of the formula

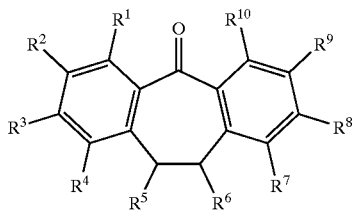

in which
R$^1$ to R$^{10}$ are each as defined above, in the presence of from 0.001 to 30% by weight, based on the starting material, of a catalyst comprising 0.5 to 15% by weight of an element of the 8th transition group, which is optionally supported, and from 0.2 to 10 parts by weight, based on one part by weight of starting material, of α,β-unsaturated carbonyl compounds as hydrogen acceptors.

10. A process as in claim 9, wherein said step of catalytically dehydrogenating dibenzosuberones is carried out in the presence of from 0.2 to 15% by weight, based on the starting material, of a catalyst comprising 0.5 to 15% by weight of an element of the 8th transition group.

11. A process as in claim 9, wherein said step of catalytically dehydrogenating dibenzosuberones is carried out in the presence of from 0.001 to 30% by weight, based on the starting material, of a catalyst comprising 1 to 10% by weight of an element of the 8th transition group.

12. A process as in claim 9, wherein said step of catalytically dehydrogenating dibenzosuberones is carried out in the presence of from 0.2 to 15% by weight, based on the starting material, of a catalyst comprising 1 to 10% by weight of an element of the 8th transition group.

13. A process for preparing substituted dibenzosuberenones of the formula

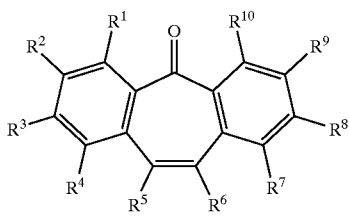

in which

R$^1$ to R$^{10}$ are identical or different and represent hydrogen, fluorine, chlorine, bromine, cyano, iodine, a straight-chain or branched aliphatic hydrocarbon radical having 1 to 8 carbon atoms, a straight-chain or branched acyl radical having 1 to 8 carbon atoms, a substituted aryl radical, a substituted hetaryl radical, or one of the groups

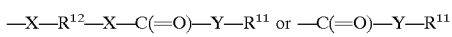

in which

R$^{11}$ represents a straight-chain or branched alkyl radical having 1 to 8 carbon atoms, R$^{12}$ represents a straight-chain or branched alkyl radical or acyl radical having 1 to 8 carbon atoms and X and Y are identical or different and represent

where

R$^{13}$ represents a straight-chain or branched alkyl radical having 1 to 8 carbon atoms, comprising the step of catalytically dehydrogenating dibenzosuberones of the formula

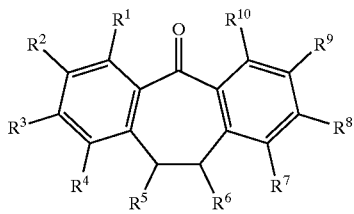

in which

R$^1$ to R$^{10}$ are each as defined above, in the presence of from 0.001 to 5% by weight, based on the starting material, of a catalyst comprising an element of the 8th transition group, which is optionally supported, and from 0.2 to 10 parts by weight, based on one part by weight of starting material, of α,β-unsaturated carbonyl compounds as hydrogen acceptors.

14. A process as in claim 1, wherein the dehydrogenated product is recrystallized using ethanol.

* * * * *